US010669324B2

(12) United States Patent
Sondermann et al.

(10) Patent No.: US 10,669,324 B2
(45) Date of Patent: *Jun. 2, 2020

(54) VECTOR ENCODING AN FC GAMMA RECEPTOR IIB PROTEIN AND COMPOSITION OF THE ENCODED PROTEIN

(71) Applicant: SUPPREMOL GMBH, Munich (DE)

(72) Inventors: Peter Sondermann, Stockdorf (DE); Dominik Ter Meer, Munich (DE); Thomas Pohl, Neuried (DE); Reno Winter, Oderwitz (DE); Uwe Jacob, Munich (DE)

(73) Assignee: SUPPREMOL GMBH, Munich (DE)

( * ) Notice: Subject to any disclaimer, the term of this patent is extended or adjusted under 35 U.S.C. 154(b) by 9 days.

This patent is subject to a terminal disclaimer.

(21) Appl. No.: 14/439,493

(22) PCT Filed: Oct. 30, 2013

(86) PCT No.: PCT/EP2013/072741
§ 371 (c)(1),
(2) Date: Apr. 29, 2015

(87) PCT Pub. No.: WO2014/068012
PCT Pub. Date: May 8, 2014

(65) Prior Publication Data
US 2015/0274804 A1    Oct. 1, 2015

Related U.S. Application Data

(63) Continuation-in-part of application No. 13/663,527, filed on Oct. 30, 2012, now Pat. No. 10,028,998.

(51) Int. Cl.
*C12N 15/09* (2006.01)
*C07K 14/735* (2006.01)
*A61K 38/00* (2006.01)

(52) U.S. Cl.
CPC ........ *C07K 14/70535* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 6,849,719 B2 * | 2/2005 | Shi | ......................... | C07K 14/54 435/69.7 |
| 7,504,482 B2 * | 3/2009 | Sondermann | .... | C07K 14/70535 530/350 |
| 8,853,363 B2 * | 10/2014 | Huber | .................. | C07K 16/283 530/387.1 |
| 2005/0002924 A1 | 1/2005 | Huber et al. | | |
| 2007/0207163 A1 * | 9/2007 | Sondermann | .... | C07K 14/70535 424/185.1 |
| 2008/0014141 A1 * | 1/2008 | Huber | .............. | C07K 14/70535 424/9.1 |
| 2014/0120080 A1 | 5/2014 | Buckel et al. | | |
| 2016/0185857 A1 | 6/2016 | Sondermann et al. | | |
| 2017/0226208 A1 | 8/2017 | Carle et al. | | |

FOREIGN PATENT DOCUMENTS

| | | |
|---|---|---|
| EP | 1 870 422 A1 * | 12/2007 |
| WO | 2000/032767 A1 | 6/2000 |
| WO | 2003/043648 A2 | 5/2003 |
| WO | 2004/016750 A2 | 2/2004 |
| WO | 2005/051999 A2 | 6/2005 |
| WO | 2007/068047 A1 | 6/2007 |
| WO | 2009/062690 A1 | 5/2009 |
| WO | 2009/083009 A2 | 7/2009 |
| WO | 2009/158696 A1 | 12/2009 |
| WO | 2014/068012 A1 | 5/2014 |
| WO | 2015/022077 A1 | 2/2015 |

OTHER PUBLICATIONS

SuppreMol Press Release—SuppreMol initiates Phase Ib/IIa clinical trial with its lead candidate SM101 (Apr. 12, 2010).*
Sondermann et al. Human Fcgamma receptor IIb expressed in *Escherichia coli* reveals IgG binding capability. Biol Chem. Jun. 1999; 380(6):717-21.*
Ahn et al., Long-term danazol therapy in autoimmune thrombocytopenia: unmaintained remission and age-dependent response in women. Annals of Internal Medicine, vol. 111, pp. 723-729 (1989).
Baccarani et al., Splenectomy in hematology. Current practice and new perspectives. Haematologica, vol. 84, pp. 431-436 (1999).
Berchtold et al., Therapy of chronic idiopathic thrombocytopenic purpura in adults. Blood, vol. 74, No. 7, pp. 2309-2317 (Nov. 15, 1989).
Brighton et al., Prospective evaluation of the clinical usefulness of an antigen-specific assay (MAIPA) in the idiopathic thrombocytopenic purpura and other immune thrombocytopenias. Blood, vol. 88, No. 1, pp. 194-201 (1996).
Burzynski, Julianna, New options after first-line therapy for chronic immune thrombocytopenic purpura. American Journal of Health-System Pharmacy, vol. 66, Suppl. 2, pp. S11-S21 (2009).
Cines et al., How I treat idiopathic thrombocytopenic purpura (ITP). Blood, vol. 106, No. 7, pp. 2244-2251 (2005).

(Continued)

*Primary Examiner* — Dong Jiang
(74) *Attorney, Agent, or Firm* — K&L Gates LLP; Louis C. Cullman; Hal Gibson

(57) ABSTRACT

The present invention relates to a nucleic acid sequence which encodes a protein of SEQ ID NO: 1; a vector comprising said nucleic acid sequence and a host cell comprising said nucleic acid sequence or said vector. The present invention also relates to a protein obtained or obtainable by expression of said nucleic acid sequence or said vector in a host cell. Furthermore, the present invention relates to a protein encoded by a nucleic acid sequence of SEQ ID NO: 6. Additionally comprised by the present invention are pharmaceutical compositions and a method of manufacturing the same.

8 Claims, 2 Drawing Sheets
Specification includes a Sequence Listing.

(56) References Cited

OTHER PUBLICATIONS

Clinical trial ISRCTN47912914, A phase Ib/IIa clinical trial to investigate the safety and efficacy of recombinant human soluble Fc-gamma receptor IIb (SM101) for intravenous application in the treatment of patients with chronic adult idiopathic thrombocytopenic purpura (ITP). ISRCTN Registry, last edited Apr. 19, 2011.
Commmittee for orphan medicinal Products: Public summary of positive opinion for orphan designation of recombinant human soluble FC-gamma receptor II b for the treatment of idiopathic thrombocytopenic purpura. European Medicines Agnecy, Pre-authorisation Evaluation of Medicines for Human Use (© EMEA, 2008) (Aug. 2, 2007, orphan designation (EU/3/07/462) was granted by the European Commission to SuppreMol GmbH, Germany, for recombinant human soluble Fc-gamma receptor II b for the treatment of idiopathic thrombocytopenic purpura, 4 pages).
Ellsworth et al., Recombinant soluble human FcγR1A (CD64A) reduces inflammation in murine collagen-induced arthritis. The Journal of Immunology, 182:7272-7279 (2009).
Ellsworth et al.,Targeting immune complex-mediated hypersensitivity with recombinant soluble human FcγRIA (CD64A). The Journal of Immunology, 180:580-589 (2008).
EU Clinical Trials Register, A randomised, multi-centre, double-blind, placebo-controlled, single/multiple dose escalation phase Ib/IIa clinical trial to investigate the safety and efficacy of recombinant human soluble Fc-gamma receptor IIb (SM101) for intravenous application in the treatment of patients with chronic adult idiopathic thrombocytopenic purpura (ITP) (Sep. 14, 2009).
Feudjo-Tepie et al., Prevalence of diagnosed chronic immune thrombocytopenic purpura in the US: analysis of a Large US claim database: a rebuttal. Journal of Thrombosis and Haemostasis, vol. 6, pp. 711-712 (2008).
George et al., Idiopathic thrombocytopenic purpura: A practice guideline developed by explicit methods for the American Society of Hematology. Blood, vol. 88, No. 1, pp. 3-40 (1996).
Godeau et al., Dapsone for chronic autoimmune thrombocytopenic purpura: a report of 66 cases. British Journal of Haematology, vol. 97, pp. 336-339 (1997).
Godeau et al., Treatment of adult chronic autoimmune thrombocytopenic purpura with repeated high-dose intravenous immunoglobulin. Blood, vol. 82, No. 5, pp. 1415-1421 (1993).
Guidelines for the investigation and management of idiopathic thrombocytopenic purpura in adults, children and in pregnancy. British Journal of Haematology, vol. 120, pp. 574-596 (2003).
International Search Report for International Application No. PCT/EP2013/072741 filed on Oct. 30, 2013.
Magnusson et al., Amelioration of collagen-induced arthritis by human recombinant soluble FCγRIIb. Clinical Immunology, 127:225-233 (2008).
Provan et al., Efficacy of mycophenolate mofetil as single-agent therapy for refractory immune thrombocytopenic purpura. American Journal of Hematology, vol. 81, pp. 19-25 (2006).
Rodeghiero et al., Standardization of terminology, definitions and outcome criteria in immune thrombocytopenia of adults and children: report of an international working group. Blood, vol. 113, No. 11, pp. 2386-2393 (2009).
Scaradavou et al., Intravenous anti-D treatment of immune thrombocytopenic purpura: experience in 272 patients. Blood, vol. 89, No. 8, pp. 2689-2700 (1997).
Segal et al., Prevalence of immune thrombocytopenia: analyses of administrative data. Journal of Thrombosis and Haemostasis, vol. 4, pp. 2377-2383 (2006).
SuppreMol Press Release, SuppreMol releases positive interim phase Ib/IIa results on SM101 in primary immune thrombocytopenia (ITP) trials (Feb. 14, 2012, Munich, Germany).
SuppreMol Press Release: SuppreMol initiates Phase IIa clinical trial in Systemic Lupus Erythematosus (SLE) with its lead candidate SM101 (Jul. 11, 2011).
SuppreMol Press Release: SuppreMol Completes Successful Pre-IND meeting with FDA. (Munich, Germany, Jan. 24, 2011).
International Search Report and Written Opinion for International Application No. PCT/EP2014/002234 filed on Aug. 13, 2014.
Janeway et al., Immunology Third Edition, Garland Publishing Inc. 1997, Chapter 3, Structure of the Antibody Molecule and Immunoglobulin Genes, pp. 122-123 (1997).
Mathey et al., Commentary: Sorting the wheat from the chaff: identifying demyelinating components of the myelin oligodendrocyte glycoprotein (MOG)-specific autoantibody repertoire. Eur. J. Immunol., 34:2065-2071 (2004).
Rudikoff et al., Single amino acid substitution altering antigen-binding specificity. PNAS, vol. 79, pp. 1979-1983 (1982).

* cited by examiner

FIGURE 1 a)

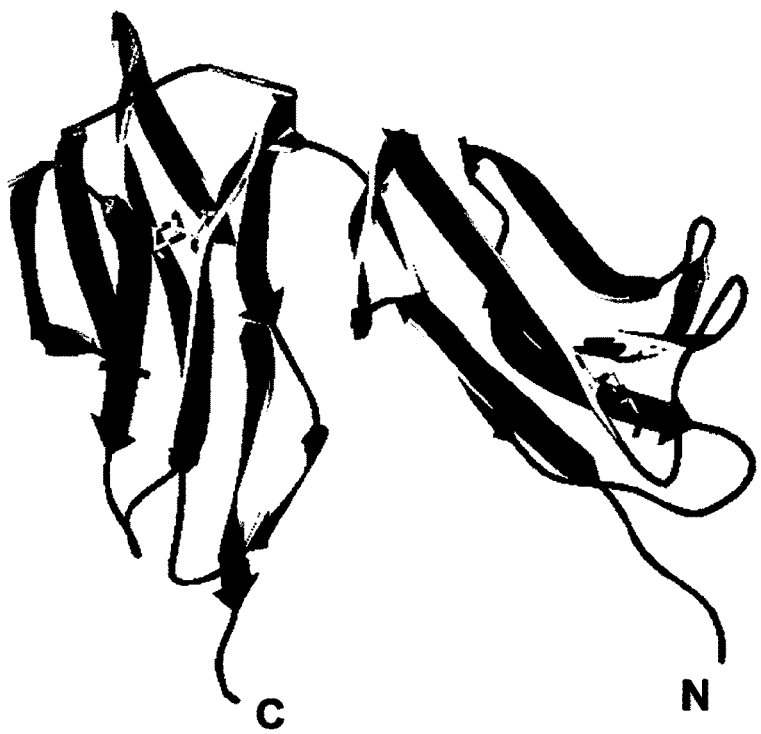

b)

```
Seq.7: "var.1"    --------MAVLKLEPQWINVLQEDSVTLTCRGTHSPESDSIQWFHNGNLIPTHTQPSYR
Seq.8: "var.2"    MGTPAAPPKAVLKLEPQWINVLQEDSVTLTCRGTHSPESDSIQWFHNGNLIPTHTQPSYR
Seq.1: "var.3"    ----MAPPKAVLKLEPQWINVLQEDSVTLTCRGTHSPESDSIQWFHNGNLIPTHTQPSYR
Seq.9: "var.4"    -MTPAAPPKAVLKLEPQWINVLQEDSVTLTCRGTHSPESDSIQWFHNGNLIPTHTQPSYR
                          ******************************************************

Seq.7: "var.1"    FKANNNDSGEYTCQTGQTSLSDPVHLTVLSEWLVLQTPHLEFQEGETIVLRCHSWKDKPL
Seq.8: "var.2"    FKANNNDSGEYTCQTGQTSLSDPVHLTVLSEWLVLQTPHLEFQEGETIVLRCHSWKDKPL
Seq.1: "var.3"    FKANNNDSGEYTCQTGQTSLSDPVHLTVLSEWLVLQTPHLEFQEGETIVLRCHSWKDKPL
Seq.9: "var.4"    FKANNNDSGEYTCQTGQTSLSDPVHLTVLSEWLVLQTPHLEFQEGETIVLRCHSWKDKPL
                  ***********************************************************

Seq.7: "var.1"    VKVTFFQNGKSKKFSRSDPNFSIPQANHSHSGDYHCTGNIGYTLYSSKPVTITV------
Seq.8: "var.2"    VKVTFFQNGKSKKFSRSDPNFSIPQANHSHSGDYHCTGNIGYTLYSSKPVTITVQAPSSS
Seq.1: "var.3"    VKVTFFQNGKSKKFSRSDPNFSIPQANHSHSGDYHCTGNIGYTLYSSKPVTITVQAPSSS
Seq.9: "var.4"    VKVTFFQNGKSKKFSRSDPNFSIPQANHSHSGDYHCTGNIGYTLYSSKPVTITVQAPSSS
                  *****************************************************

Seq.7: "var.1"    -----
Seq.8: "var.2"    PMGII
Seq.1: "var.3"    P----
Seq.9: "var.4"    PMGI-
```

FIGURE 2
pH 6
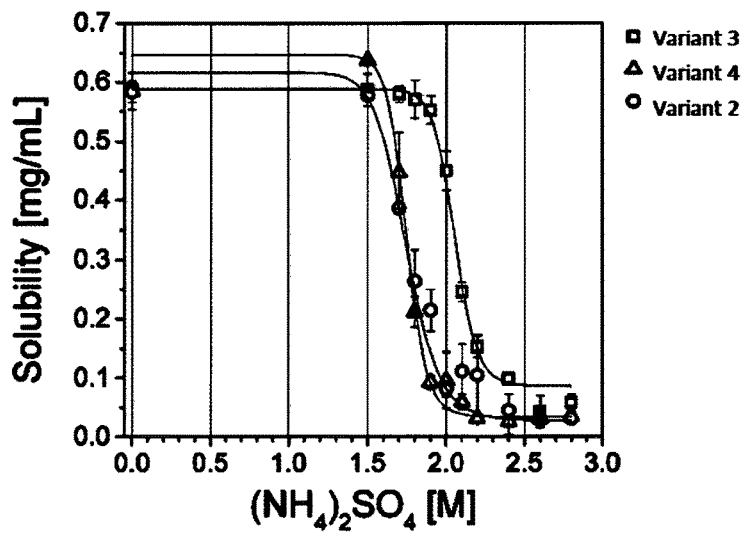
pH 7
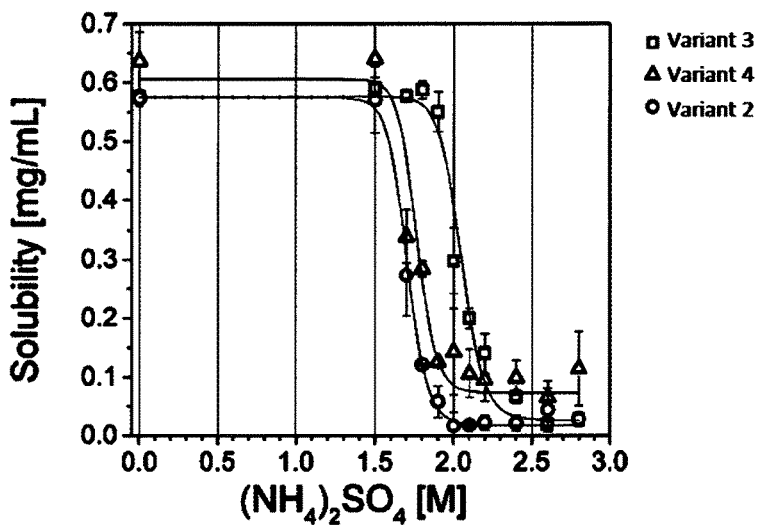
pH 8
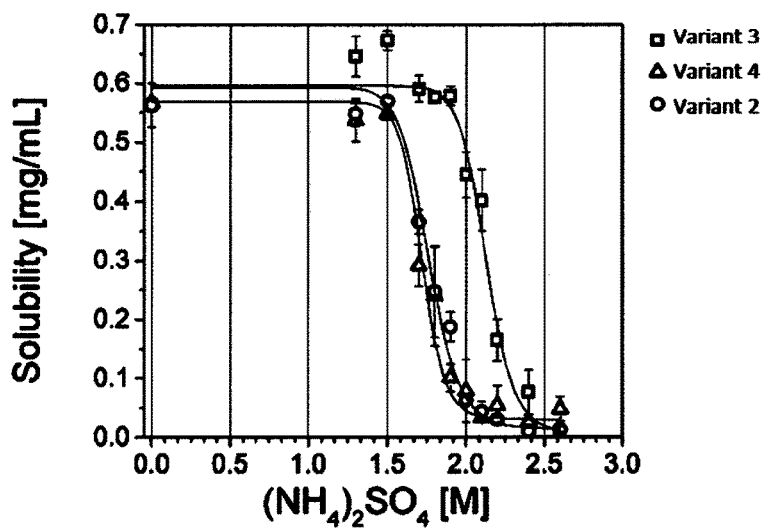

SEQUENCE LISTING

```
<160> NUMBER OF SEQ ID NOS: 9

<210> SEQ ID NO 1
<211> LENGTH: 177
<212> TYPE: PRT
<213> ORGANISM: artificial
<220> FEATURE:
<223> OTHER INFORMATION: Fc gamma receptor IIB variant

<400> SEQUENCE: 1

Met Ala Pro Pro Lys Ala Val Leu Lys Leu Glu Pro Gln Trp Ile Asn
1               5                   10                  15

Val Leu Gln Glu Asp Ser Val Thr Leu Thr Cys Arg Gly Thr His Ser
            20                  25                  30

Pro Glu Ser Asp Ser Ile Gln Trp Phe His Asn Gly Asn Leu Ile Pro
        35                  40                  45

Thr His Thr Gln Pro Ser Tyr Arg Phe Lys Ala Asn Asn Asn Asp Ser
    50                  55                  60

Gly Glu Tyr Thr Cys Gln Thr Gly Gln Thr Ser Leu Ser Asp Pro Val
65                  70                  75                  80

His Leu Thr Val Leu Ser Glu Trp Leu Val Leu Gln Thr Pro His Leu
                85                  90                  95

Glu Phe Gln Glu Gly Glu Thr Ile Val Leu Arg Cys His Ser Trp Lys
            100                 105                 110

Asp Lys Pro Leu Val Lys Val Thr Phe Phe Gln Asn Gly Lys Ser Lys
        115                 120                 125

Lys Phe Ser Arg Ser Asp Pro Asn Phe Ser Ile Pro Gln Ala Asn His
    130                 135                 140

Ser His Ser Gly Asp Tyr His Cys Thr Gly Asn Ile Gly Tyr Thr Leu
145                 150                 155                 160

Tyr Ser Ser Lys Pro Val Thr Ile Thr Val Gln Ala Pro Ser Ser Ser
                165                 170                 175

Pro

<210> SEQ ID NO 2
<211> LENGTH: 176
<212> TYPE: PRT
<213> ORGANISM: artificial
<220> FEATURE:
<223> OTHER INFORMATION: Fc gamma receptor IIB variant

<400> SEQUENCE: 2
```

```
Ala Pro Pro Lys Ala Val Leu Lys Leu Glu Pro Gln Trp Ile Asn Val
1               5                   10                  15

Leu Gln Glu Asp Ser Val Thr Leu Thr Cys Arg Gly Thr His Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
        115                 120                 125

Phe Ser Arg Ser Asp Pro Asn Phe Ser Ile Pro Gln Ala Asn His Ser
130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln Ala Pro Ser Ser Ser Pro
                165                 170                 175

<210> SEQ ID NO 3
<211> LENGTH: 175
<212> TYPE: PRT
<213> ORGANISM: artificial
<220> FEATURE:
<223> OTHER INFORMATION: Fc gamma receptor IIB variant

<400> SEQUENCE: 3

Pro Pro Lys Ala Val Leu Lys Leu Glu Pro Gln Trp Ile Asn Val Leu
1               5                   10                  15

Gln Glu Asp Ser Val Thr Leu Thr Cys Arg Gly Thr His Ser Pro Glu
            20                  25                  30

Ser Asp Ser Ile Gln Trp Phe His Asn Gly Asn Leu Ile Pro Thr His
        35                  40                  45

Thr Gln Pro Ser Tyr Arg Phe Lys Ala Asn Asn Asn Asp Ser Gly Glu
    50                  55                  60

Tyr Thr Cys Gln Thr Gly Gln Thr Ser Leu Ser Asp Pro Val His Leu
65                  70                  75                  80

Thr Val Leu Ser Glu Trp Leu Val Leu Gln Thr Pro His Leu Glu Phe
                85                  90                  95

Gln Glu Gly Glu Thr Ile Val Leu Arg Cys His Ser Trp Lys Asp Lys
            100                 105                 110

Pro Leu Val Lys Val Thr Phe Phe Gln Asn Gly Lys Ser Lys Lys Phe
        115                 120                 125

Ser Arg Ser Asp Pro Asn Phe Ser Ile Pro Gln Ala Asn His Ser His
130                 135                 140

Ser Gly Asp Tyr His Cys Thr Gly Asn Ile Gly Tyr Thr Leu Tyr Ser
145                 150                 155                 160

Ser Lys Pro Val Thr Ile Thr Val Gln Ala Pro Ser Ser Ser Pro
                165                 170                 175

<210> SEQ ID NO 4
```

<211> LENGTH: 174
<212> TYPE: PRT
<213> ORGANISM: artificial
<220> FEATURE:
<223> OTHER INFORMATION: Fc gamma receptor IIB variant

<400> SEQUENCE: 4

```
Pro Lys Ala Val Leu Lys Leu Glu Pro Gln Trp Ile Asn Val Leu Gln
1               5                   10                  15

Glu Asp Ser Val Thr Leu Thr Cys Arg Gly Thr His Ser Pro Glu Ser
            20                  25                  30

Asp Ser Ile Gln Trp Phe His Asn Gly Asn Leu Ile Pro Thr His Thr
        35                  40                  45

Gln Pro Ser Tyr Arg Phe Lys Ala Asn Asn Asn Asp Ser Gly Glu Tyr
    50                  55                  60

Thr Cys Gln Thr Gly Gln Thr Ser Leu Ser Asp Pro Val His Leu Thr
65                  70                  75                  80

Val Leu Ser Glu Trp Leu Val Leu Gln Thr Pro His Leu Glu Phe Gln
                85                  90                  95

Glu Gly Glu Thr Ile Val Leu Arg Cys His Ser Trp Lys Asp Lys Pro
            100                 105                 110

Leu Val Lys Val Thr Phe Phe Gln Asn Gly Lys Ser Lys Lys Phe Ser
        115                 120                 125

Arg Ser Asp Pro Asn Phe Ser Ile Pro Gln Ala Asn His Ser His Ser
    130                 135                 140

Gly Asp Tyr His Cys Thr Gly Asn Ile Gly Tyr Thr Leu Tyr Ser Ser
145                 150                 155                 160

Lys Pro Val Thr Ile Thr Val Gln Ala Pro Ser Ser Ser Pro
                165                 170
```

<210> SEQ ID NO 5
<211> LENGTH: 172
<212> TYPE: PRT
<213> ORGANISM: artificial
<220> FEATURE:
<223> OTHER INFORMATION: Fc gamma receptor IIB variant

<400> SEQUENCE: 5

```
Ala Val Leu Lys Leu Glu Pro Gln Trp Ile Asn Val Leu Gln Glu Asp
1               5                   10                  15

Ser Val Thr Leu Thr Cys Arg Gly Thr His Ser Pro Glu Ser Asp Ser
            20                  25                  30

Ile Gln Trp Phe His Asn Gly Asn Leu Ile Pro Thr His Thr Gln Pro
        35                  40                  45

Ser Tyr Arg Phe Lys Ala Asn Asn Asn Asp Ser Gly Glu Tyr Thr Cys
    50                  55                  60

Gln Thr Gly Gln Thr Ser Leu Ser Asp Pro Val His Leu Thr Val Leu
65                  70                  75                  80

Ser Glu Trp Leu Val Leu Gln Thr Pro His Leu Glu Phe Gln Glu Gly
                85                  90                  95

Glu Thr Ile Val Leu Arg Cys His Ser Trp Lys Asp Lys Pro Leu Val
            100                 105                 110

Lys Val Thr Phe Phe Gln Asn Gly Lys Ser Lys Lys Phe Ser Arg Ser
        115                 120                 125

Asp Pro Asn Phe Ser Ile Pro Gln Ala Asn His Ser His Ser Gly Asp
    130                 135                 140

Tyr His Cys Thr Gly Asn Ile Gly Tyr Thr Leu Tyr Ser Ser Lys Pro
```

```
                  145                 150                 155                 160
Val Thr Ile Thr Val Gln Ala Pro Ser Ser Pro
                165                 170

<210> SEQ ID NO 6
<211> LENGTH: 534
<212> TYPE: DNA
<213> ORGANISM: artificial
<220> FEATURE:
<223> OTHER INFORMATION: Fc gamma receptor IIB variant

<400> SEQUENCE: 6
atggcaccgc cgaaagcagt tctgaaactg gaaccgcagt ggattaacgt tctgcaggaa      60
gatagcgtta ccctgacctg tcgtggcacc catagcccgg aaagcgatag cattcagtgg     120
tttcacaacg gcaatctgat tccgacccat acccagccga gctatcgttt taaagcgaac     180
aacaacgata gcggcgaata tacctgtcag accggtcaga ccagcctgag cgatccggtt     240
catctgaccg ttctgagcga atggctggtt ctgcagaccc cgcatctgga atttcaggaa     300
ggcgaaacca ttgttctgcg ttgccacagc tggaaagata aaccgctggt taaagttacc     360
ttcttccaga acggcaaaag caaaaaattc agccgtagcg atccgaattt tagcattccg     420
caggcgaatc atagccatag cggcgattat cattgtaccg gcaacattgg ctataccctg     480
tatagcagca aaccggtgac cattaccgtt caggcgccga gcagcagccc gtaa           534

<210> SEQ ID NO 7
<211> LENGTH: 166
<212> TYPE: PRT
<213> ORGANISM: artificial
<220> FEATURE:
<223> OTHER INFORMATION: Fc gamma receptor IIB variant

<400> SEQUENCE: 7

Met Ala Val Leu Lys Leu Glu Pro Gln Trp Ile Asn Val Leu Gln Glu
1               5                   10                  15

Asp Ser Val Thr Leu Thr Cys Arg Gly Thr His Ser Pro Glu Ser Asp
            20                  25                  30

Ser Ile Gln Trp Phe His Asn Gly Asn Leu Ile Pro Thr His Thr Gln
        35                  40                  45

Pro Ser Tyr Arg Phe Lys Ala Asn Asn Asn Asp Ser Gly Glu Tyr Thr
    50                  55                  60

Cys Gln Thr Gly Gln Thr Ser Leu Ser Asp Pro Val His Leu Thr Val
65                  70                  75                  80

Leu Ser Glu Trp Leu Val Leu Gln Thr Pro His Leu Glu Phe Gln Glu
                85                  90                  95

Gly Glu Thr Ile Val Leu Arg Cys His Ser Trp Lys Asp Lys Pro Leu
            100                 105                 110

Val Lys Val Thr Phe Phe Gln Asn Gly Lys Ser Lys Lys Phe Ser Arg
        115                 120                 125

Ser Asp Pro Asn Phe Ser Ile Pro Gln Ala Asn His Ser His Ser Gly
    130                 135                 140

Asp Tyr His Cys Thr Gly Asn Ile Gly Tyr Thr Leu Tyr Ser Ser Lys
145                 150                 155                 160

Pro Val Thr Ile Thr Val
                165

<210> SEQ ID NO 8
<211> LENGTH: 185
```

```
<212> TYPE: PRT
<213> ORGANISM: artificial
<220> FEATURE:
<223> OTHER INFORMATION: Fc gamma receptor IIB variant

<400> SEQUENCE: 8

Met Gly Thr Pro Ala Ala Pro Pro Lys Ala Val Leu Lys Leu Glu Pro
1               5                   10                  15

Gln Trp Ile Asn Val Leu Gln Glu Asp Ser Val Thr Leu Thr Cys Arg
            20                  25                  30

Gly Thr His Ser Pro Glu Ser Asp Ser Ile Gln Trp Phe His Asn Gly
        35                  40                  45

Asn Leu Ile Pro Thr His Thr Gln Pro Ser Tyr Arg Phe Lys Ala Asn
    50                  55                  60

Asn Asn Asp Ser Gly Glu Tyr Thr Cys Gln Thr Gly Gln Thr Ser Leu
65                  70                  75                  80

Ser Asp Pro Val His Leu Thr Val Leu Ser Glu Trp Leu Val Leu Gln
                85                  90                  95

Thr Pro His Leu Glu Phe Gln Glu Gly Glu Thr Ile Val Leu Arg Cys
            100                 105                 110

His Ser Trp Lys Asp Lys Pro Leu Val Lys Val Thr Phe Phe Gln Asn
        115                 120                 125

Gly Lys Ser Lys Lys Phe Ser Arg Ser Asp Pro Asn Phe Ser Ile Pro
130                 135                 140

Gln Ala Asn His Ser His Ser Gly Asp Tyr His Cys Thr Gly Asn Ile
145                 150                 155                 160

Gly Tyr Thr Leu Tyr Ser Ser Lys Pro Val Thr Ile Thr Val Gln Ala
                165                 170                 175

Pro Ser Ser Ser Pro Met Gly Ile Ile
            180                 185

<210> SEQ ID NO 9
<211> LENGTH: 183
<212> TYPE: PRT
<213> ORGANISM: artificial
<220> FEATURE:
<223> OTHER INFORMATION: Fc gamma receptor IIB variant

<400> SEQUENCE: 9

Met Thr Pro Ala Ala Pro Pro Lys Ala Val Leu Lys Leu Glu Pro Gln
1               5                   10                  15

Trp Ile Asn Val Leu Gln Glu Asp Ser Val Thr Leu Thr Cys Arg Gly
            20                  25                  30

Thr His Ser Pro Glu Ser Asp Ser Ile Gln Trp Phe His Asn Gly Asn
        35                  40                  45

Leu Ile Pro Thr His Thr Gln Pro Ser Tyr Arg Phe Lys Ala Asn Asn
    50                  55                  60

Asn Asp Ser Gly Glu Tyr Thr Cys Gln Thr Gly Gln Thr Ser Leu Ser
65                  70                  75                  80

Asp Pro Val His Leu Thr Val Leu Ser Glu Trp Leu Val Leu Gln Thr
                85                  90                  95

Pro His Leu Glu Phe Gln Glu Gly Glu Thr Ile Val Leu Arg Cys His
            100                 105                 110

Ser Trp Lys Asp Lys Pro Leu Val Lys Val Thr Phe Phe Gln Asn Gly
        115                 120                 125

Lys Ser Lys Lys Phe Ser Arg Ser Asp Pro Asn Phe Ser Ile Pro Gln
130                 135                 140
```

```
Ala Asn His Ser His Ser Gly Asp Tyr His Cys Thr Gly Asn Ile Gly
145                 150                 155                 160

Tyr Thr Leu Tyr Ser Ser Lys Pro Val Thr Ile Thr Val Gln Ala Pro
                165                 170                 175

Ser Ser Ser Pro Met Gly Ile
            180
```

VECTOR ENCODING AN FC GAMMA RECEPTOR IIB PROTEIN AND COMPOSITION OF THE ENCODED PROTEIN

FIELD OF THE INVENTION

The present invention relates to a nucleic acid sequence which encodes a protein of SEQ ID NO: 1; a vector comprising said nucleic acid sequence and a host cell comprising said nucleic acid sequence or said vector. The present invention also relates to a protein obtained or obtainable by expression of said nucleic acid sequence or said vector in a host cell. Furthermore, the present invention relates to a protein encoded by a nucleic acid sequence of SEQ ID NO: 6. Additionally comprised by the present invention are pharmaceutical compositions and a method of manufacturing the same. The present invention further relates to a composition of matter comprising a protein according to SEQ ID NO: 2 and/or 3, which composition may further comprise a protein according to SEQ ID NO: 4 and/or 5.

BACKGROUND

FcγRs belong to the family of Fc receptors (FcRs) which are crucial for defending the human organism against infections. In general, activating FcγRs and inhibiting FcγRs are to be distinguished. Of the three main FcγRs in humans, FcγRI can bind monomeric IgG, whereas FcγRII and FcγRIII bind to multivalent immune complexes (ICs) composed of antibodies and antigens (Takai, T. Nature Reviews Immunology 2002: 580-592.). Effector functions triggered by FcγRs include, depending on the expressed FcR type and associated proteins, endocytosis with subsequent neutralization of the pathogens and antigen presentation, antibody-dependent cellular cytotoxity (ADCC), secretion of mediators or the regulation of antibody production (Fridman et al. Immunol Rev. 1992125:49-76, van de Winkel and Capel Immunol Today. 1993: 14(5):215-21).

WO 00/32767 describes soluble Fc receptors (FcRs) which are composed of only the extracellular part of the receptor and are not glycosylated. Due to the absence of the transmembrane domain and of the signal peptide, these proteins are present in a soluble form and not bound to cells. Furthermore the FcRs described in WO 00/32767 can be produced recombinantly and have been suggested for the treatment of autoimmune diseases due to their ability to bind the Fc part of antibodies without interfering with other components of the immune system. WO 00/32767 additionally describes the crystal structure of certain FcRs and the possibility of finding substances that inhibit the interaction of IgG with FcRs with the aid of these crystal structures. The elucidation of the crystal structure enables the finding of such inhibitors by screening the databases using available computer programs. The invention which as defined in WO 03/043648 further developed the findings of WO 00/32767 and provides treatment methods especially for diseases like multiple sclerosis (MS), systemic lupus erythematosus (SLE), and rheumatoid arthritis (RA) and also for diseases with an elevated level of natural killer cells.

When said receptors were produced recombinantly in prokaryotes and therefore were unglycosylated the inventors of WO 03/043648 surprisingly found that although the unglycosylated proteins were expected to be poorly soluble, the receptors could be purified with high concentrations of FcγR in a soluble form. WO 03/043648 and other publications document that FcRs play an important role in defense reactions of the immune system.

Fc receptors play a central role in the immune system where they control the extent and strength of an immune response. It turned out that in particular a soluble (i.e. the extracellular part of a Fc gamma receptor IIB) Fc gamma receptor IIB (sFcγRIIB), which competes with FcγRs expressed on immune cells for pathogenic immune complexes is beneficial in the treatment of autoimmune diseases. Interference at an early stage of the immune reactions that take place in autoimmune diseases prevents the triggering of the cascade that results in inflammation and tissue destruction. Specifically, meanwhile sFcγRIIB is in phase II clinical trials for the indication Primary Immune Thrombocytopenia (ITP) and Systemic Lupus Erythematosus (SLE). As is commonly known, for clinical trials biological material, here sFcγRIIB is needed that has preferably good Chemistry, Manufacturing and Control (CMC) properties, such as high purity and stability during purification.

Thus it was an object of the present invention to provide human FcγRIIB proteins with good CMC properties. This object is solved by the embodiments reflected in the claims, described herein, illustrated in the Examples and Figures.

Surprisingly it has been shown for the proteins such as those described herein, that higher purification can be achieved due to better solubility at ammonium sulfate concentrations exceeding 1.5M. Ammonium sulfate precipitation is useful to remove large amounts of contaminant proteins, as a first step in many purification schemes. The higher the ammonium sulfate concentration, the better it is when aiming at a highly pure protein, but the more stress is posed upon the protein, because of the high ionic strength of ammonium sulfate. Thus, the more stress resistant a protein is, the higher can be the ammonium sulfate concentration and thus the higher will be the purity of the protein. Specifically, by the addition of the kosmotropic ammonium sulfate byproducts such as unfolded and misfolded species but also host cell derived impurities like cell wall components and proteins are precipitated. With increasing precipitant concentration the precipitation efficiency will be increased and hence a highly purified protein preparation is obtained as long as the protein of interest is resistant to precipitation at such high ammonium sulfate concentrations. As said, it surprisingly turned out that a FcR protein as described herein is highly soluble at ammonium sulfate concentrations equal to or exceeding 1.5 M. This could not have been expected, since prior art FcR proteins behaved differently as is shown in the Examples and there was no guidance whatsoever available as how to modify a FcR protein such that it has the behavior and properties as the FcR protein provided by the present invention. As said, much to the surprise of the present inventors, it turned out that the proteins described herein are indeed resistant to high ammonium sulfate concentrations, thereby allowing a good purification in comparison to prior art FcγRIIB proteins, such as FcγRIIB proteins described in WO 00/32767 or WO 03/043648.

BRIEF DESCRIPTION OF THE INVENTION

The present invention relates to a nucleic acid sequence which encodes a protein according to SEQ ID No: 1. The present invention also provide nucleic acid sequences encoding the proteins shown in SEQ ID NO: 2, 3, 4, 5, or 9. The nucleic acid sequence shown in SEQ ID NO: 6 encodes the protein according to SEQ ID NO: 1.

The present invention also relates to a vector comprising the nucleic acid sequence which encodes the protein according to SEQ ID NO: 1. The present invention also relates to a vector comprising the nucleic acid sequence which encodes the protein according to SEQ ID NO: 2, 3, 4, 5, or 9.

Further, the present invention also relates to a protein obtained or obtainable by expression of the nucleic acid sequence which encodes the protein according to SEQ ID NO: 1 or the vector of the present invention in a host cell, preferably a prokaryotic host cell, more preferably in E. coli.

In addition, the present invention also relates to a protein which is encoded by a nucleic acid sequence according to SEQ ID NO: 6.

The present invention also relates to a pharmaceutical composition comprising the protein obtained or obtainable by expression of the nucleic acid sequence which encodes the protein according to SEQ ID NO: 1 or the vector of the present invention in a host cell or a protein which is encoded by a nucleic acid sequence according to SEQ ID NO: 6.

Further, the present invention relates to a composition of matter comprising a protein according to SEQ ID No: 2 and/or 3. Preferably, the composition of matter is a pharmaceutical composition.

In one embodiment, the composition of matter of the present invention further comprises a protein according to SEQ ID No. 4 and/or 5. Preferably, the composition of matter is a pharmaceutical composition.

In another embodiment, the composition of matter of the present invention has the amount of the protein according to SEQ ID No: 2 exceeding that of the protein according to SEQ ID No: 3.

In another embodiment, the composition of matter of the present invention has the amount of the protein according to SEQ ID No: 2 exceeding that of the protein according to SEQ ID No: 3 and the amount of the proteins according to SEQ ID No: 2 and 3 exceeding that of the protein according to SEQ ID No: 4 and/or 5.

Also, the present invention relates to a composition of matter comprising a protein according to SEQ ID No: 9. Preferably, the composition of matter is a pharmaceutical composition.

The present invention also relates to a host cell comprising the nucleic acid sequence which encodes the protein according to SEQ ID NO: 1 or the host cell comprises the vector of the present invention comprising the nucleic acid sequence of claim 1. The present invention also relates to a host cell comprising a nucleic acid sequence which encodes the protein according to SEQ ID NO: 2, 3, 4, 5, or 9 or the host cell comprises the vector of the present invention comprising a nucleic acid sequence encoding the protein according to SEQ ID NO: 2, 3, 4, 5, or 9.

In one embodiment, the host cell of the present invention is a prokaryotic or eukaryotic host cell.

In another embodiment of the present invention, the prokaryotic host cell is E. coli, preferably E. coli BL21, such as BL21 (DE3)

The present invention also relates to a method of manufacturing a pharmaceutical composition comprising culturing the host cell of the present invention under conditions allowing the expression of the encoded protein, and recovering the obtained pharmaceutical composition.

FIGURES

FIG. 1: a) Crystal structure of human sFcγRIIB (PDB entry: 2FCB). The invariable core structure as represented by the amino acid sequence of variant1 (SEQ ID No: 7) which is identical for all sFcR variants tested in this study is shown in dark grey, the loops which are supposed to be important for IgG binding are depicted in light grey and the N- and C-terminal extensions are shown in black. The two disulfide bridges are depicted in ball and stick representation. The identity of the core structure between all variants tested is also apparent from the sequence alignment shown in FIG. 1b.

b) Sequence alignment of sFcR variants 1-4 (abbreviated "var.") used in this study. SEQ ID NO: was abbreviated by SEQ.

FIG. 2: Results from the FcR precipitation screen. The FcR variants 1-4 were incubated for 1 h at 25° C. and the indicated pH and ammonium sulfate concentration. After centrifugation the FcR content in the supernatant was determined by $OD_{280}$ measurement and plotted against the ammonium sulfate concentration.

SEQUENCES

The following sequences provide an overview on the sequences used herein:

```
                                              SEQ ID No: 1
MAPPKAVLKL EPQWINVLQE DSVTLTCRGT HSPESDSIQW

FHNGNLIPTH TQPSYRFKAN NNDSGEYTCQ TGQTSLSDPV

HLTVLSEWLV LQTPHLEFQE GETIVLRCHS WKDKPLVKVT

FFQNGKSKKF SRSDPNFSIP QANHSHSGDY HCTGNIGYTL

YSSKPVTITV QAPSSSP
(herein also sometimes referred to as "variant3")
                                              SEQ ID No: 2
APPKAVLKLE PQWINVLQED SVTLTCRGTH SPESDSIQWF

HNGNLIPTHT QPSYRFKANN NDSGEYTCQT GQTSLSDPVH

LTVLSEWLVL QTPHLEFQEG ETIVLRCHSW KDKPLVKVTF

FQNGKSKKFS RSDPNFSIPQ ANHSHSGDYH CTGNIGYTLY

SSKPVTITVQ APSSSP
                                              SEQ ID No: 3
PPKAVLKLEP QWINVLQEDS VTLTCRGTHS PESDSIQWFH

NGNLIPTHTQ PSYRFKANNN DSGEYTCQTG QTSLSDPVHL

TVLSEWLVLQ TPHLEFQEGE TIVLRCHSWK DKPLVKVTFF

QNGKSKKFSR SDPNFSIPQA NHSHSGDYHC TGNIGYTLYS

SKPVTITVQA PSSSP
                                              SEQ ID No: 4
PKAVLKLEPQ WINVLQEDSV TLTCRGTHSP ESDSIQWFHN

GNLIPTHTQP SYRFKANNND SGEYTCQTGQ TSLSDPVHLT

VLSEWLVLQT PHLEFQEGET IVLRCHSWKD KPLVKVTFFQ

NGKSKKFSRS DPNFSIPQAN HSHSGDYHCT GNIGYTLYSS

KPVTITVQAP SSSP
                                              SEQ ID No: 5
AVLKLEPQWI NVLQEDSVTL TCRGTHSPES DSIQWFHNGN

LIPTHTQPSY RFKANNNDSG EYTCQTGQTS LSDPVHLTVL

SEWLVLQTPH LEFQEGETIV LRCHSWKDKP LVKVTFFQNG
```

-continued

KSKKFSRSDP NFSIPQANHS HSGDYHCTGN IGYTLYSSKP

VTITVQAPSS SP

SEQ ID No: 6
atggcaccgc cgaaagcagt tctgaaactg gaaccgcagt ggattaacgt tctgcaggaa gatagcgtta ccctgacctg tcgtggcacc catagcccgg aaagcgatag cattcagtgg tttcacaacg gcaatctgat tccgacccat acccagccga gctatcgttt taaagcgaac aacaacgata gcggcgaata tacctgtcag accggtcaga ccagcctgag cgatccggtt catctgaccg ttctgagcga atggctggtt ctgcagaccc cgcatctgga atttcaggaa ggcgaaacca ttgttctgcg ttgccacagc tggaaagata aaccgctggt taaagttacc ttcttccaga acggcaaaag caaaaaattc agccgtagcg atccgaattt tagcattccg caggcgaatc atagccatag cggcgattat cattgtaccg gcaacattgg ctataccctg tatagcagca aaccggtgac cattaccgtt caggcgccga gcagcagccc gtaa

SEQ ID NO: 7
MAVLKLEPQW INVLQEDSVT LTCRGTHSPE SDSIQWFHNG

NLIPTHTQPS YRFKANNNDS GEYTCQTGQT SLSDPVHLTV

LSEWLVLQTP HLEFQEGETI VLRCHSWKDK PLVKVTFFQN

GKSKKFSRSD PNFSIPQANH SHSGDYHCTG NIGYTLYSSK

PVTITV
(herein also sometimes referred to as "variant1", this sequence is disclosed as SEQ ID NO: 1 in WO 03/043648)

SEQ 8
MGTPAAPPKA VLKLEPQWIN VLQEDSVTLT CRGTHSPESD

SIQWFHNGNL IPTHTQPSYR FKANNNDSGE YTCQTGQTSL

SDPVHLTVLS EWLVLQTPHL EFQEGETIVL RCHSWKDKPL

VKVTFFQNGK SKKFSRSDPN FSIPQANHSH SGDYHCTGNI

GYTLYSSKPV TITVQAPSSS PMGII
(herein also sometimes referred to as "variant2", this sequence is disclosed as SEQ ID NO: 3 in WO 00/32767)

SEQ ID 9
MTPAAPPKAV LKLEPQWINV LQEDSVTLTC RGTHSPESDS

IQWFHNGNLI PTHTQPSYRF KANNNDSGEY TCQTGQTSLS

DPVHLTVLSE WLVLQTPHLE FQEGETIVLR CHSWKDKPLV

KVTFFQNGKS KKFSRSDPNF SIPQANHSHS GDYHCTGNIG

YTLYSSKPVT ITVQAPSSSP MGI
(herein also sometimes referred to as "variant4")

DETAILED DESCRIPTION OF THE INVENTION

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In a first aspect, the present invention relates to a nucleic acid sequence which encodes a protein according to SEQ ID No: 1.

As used herein, the terms "nucleic acids" and "nucleotide sequences" or "nucleic acid sequence" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

A variety of modifications can be made to DNA and RNA; thus, the term "nucleic acid molecules" or "nucleic acid sequence" embraces chemically, enzymatically, or metabolically modified forms. For example, a nucleic acid molecules or a nucleic acid sequence of the present invention can be modified posttranslational or posttranscriptional.

The nucleic acid sequence of the present invention encodes the protein of SEQ ID NO: 1. The sequence of the polypeptide encoded by SEQ ID NO: 1 may be modified because of posttranslational or posttranscriptional modifications, dependent on the host cell which expresses the polypeptide encoded by SEQ ID NO: 1.

When used herein "protein of SEQ ID NO: X", with X being 1, 2, 3, 4, 5, or 9, it is meant a protein having the amino acid sequence shown or as depicted in SEQ ID NO: X, with X being 1, 2, 3, 4, 5 or 9.

The term "polypeptide" or "protein" when used herein means a peptide, a protein, or a polypeptide, which are used interchangeable and which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. As mentioned the terms polypeptide and protein are often used interchangeably herein. The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York (1983), pgs. 1-12; Seifter, Meth. Enzymol. 182 (1990); 626-646, Rattan, Ann. NY Acad. Sci. 663 (1992); 48-62.

Proteins of the present invention are shown in SEQ ID NO: 1, 2, 3, 4, 5, or 9. Thus, the present invention provides proteins shown in SEQ ID NO: 1, 2, 3, 4, 5, or 9.

The term "expression" or "expression of a nucleic acid sequence" means the transcription of a specific nucleic acid or specific genetic construct. The term "expression" or "nucleic acid expression" in particular means the transcription of a nucleic acid sequence or genetic construct like a vector comprising the nucleic acid of SEQ ID NO: 1 into structural RNA (rRNA, tRNA) or mRNA with or without subsequent translation of the latter into a protein. Preferably, the protein is then translated. The process includes transcription of DNA and processing of the resulting mRNA product. The mRNA is then translated into polypeptide chains, which are ultimately folded into the final polypeptides/proteins. Protein expression is commonly used by proteomics researchers to denote the measurement of the presence and abundance of one or more proteins in a particular cell or tissue. The expression of a protein of a cell can be measured by various means. For example, with immunohistochemistry or western blot analysis. Here the obtained results can be evaluated by a cell transfected with a vector comprising a nucleic acid of the present invention in comparison, to a mock transfected cell. A higher expressing (host) cell shows a staining, which is increased e.g. in intensity, when compared to a control cell (mock) in the same setting. Also the expression of the mRNA can be measured e.g. by RT-PCR. The person skilled in the art knows different techniques, how to determine the expression of a certain protein or mRNA of a cell. Also envisaged are proteins, obtained due to post-transcriptional or posttranslational modifications.

A "variant" of a polypeptide encompasses a polypeptide wherein one or more amino acid residues are substituted, preferably conservatively substituted compared to said polypeptide and wherein said variant is preferably able to bind to the Fc part of antibodies (see binding of FcγR) and possibly to lymphocytes. Such variants include deletions, insertions, inversions, repeats, and substitutions selected according to general rules known in the art. For example, guidance concerning how to make phenotypically silent amino acid substitutions is provided in Bowie, Science 247: (1990) 1306-1310, wherein the authors indicate that there are two main strategies for studying the tolerance of an amino acid sequence to change. Preferred variants of FcγRIIB are shown in SEQ ID NO: 1, 2, 3, 4, 5, or 9, with the FcγRIIB shown in SEQ ID NO: 1 being preferred.

The term "Fc gamma receptor" is used herein interchangeably with "FcgR" or "Fcy receptor" or "FcγR" and comprises both membranous FcγRs and soluble (i.e. the extracellular part of a Fcy receptor) FcγRs. Fc gamma receptors belong to the immunoglobulin superfamily of proteins and are found on many hematopoietic lineages. As their name indicates, Fc receptors recognize and bind to the Fc (fragment, crystallizable) part of antibodies, i.e. the fragment that corresponds to the two C-terminal domains of both heavy chains of the antibody and typically interacts with effector molecules and cells.

It is preferred that the protein according to SEQ ID NO: 1 is a soluble FcγR. Similarly, it is preferred that the protein according to SEQ ID NO: 2, 3, 4, 5, or 9 is a soluble FcγR. It is also preferred, that a protein according to SEQ ID NO: 1, 2, 3, 4, 5, or 9 is as such soluble in a suitable liquid, such as an aqueous liquid.

FcγRs recognize IgG antibodies. There are four IgG subclasses in humans, named in order of their abundance in the serum (IgG1, IgG2, IgG3, IgG4, with IgG1 being the most abundant IgG type). Three classes of FcγRs exist in humans: FcγRI (CD64), FcγRII (CD32) and FcγRIIIA (CD16). Furthermore, FcγRs occur in various isoforms, i.e. functionally similar Fc gamma receptors that have a similar but not an identical amino acid sequence. Said isoforms include FcγRIA, B1, B2, C; FcγRIIA1-2, B1-3, C and, further, several alleles (FcγRIIa1-HR, -LR; FcγRIIIb-NA1,-NA2) (van de Winkel and Capel, Immunol. Today 1993, 14:215-221). The different classes and isoforms of FcγR may differ with regard to their affinity to IgG and specifically to the different IgG subclasses. Typically, FcγR occur as type I transmembrane proteins or in soluble forms but there also exists a glycosylphosphatidylinositol anchored form of the FcγRIII (FcγRIIIB).

"Soluble FcγRs" are also referred to as "sFcγRs". As used herein, the term "soluble Fcy receptor" and analogous terms refer to the extracellular part of the Fcy receptor. Such part can be dissolved in a liquid. In general, soluble forms of any FcγR class, isoform or allele can be identified by a preceding "s", e.g., sCD32 or sFcγRII refers to the soluble Fc gamma RII receptor. Typically, in contrast to membranous (i.e., membrane-bound) FcγR, soluble FcγR do not comprise a transmembrane region or an intracytoplasmatic tail.

Preferably, the FcγR of the invention is of human origin or a human FcγR. The term "of human origin" is to be construed in its broadest sense. In general, it means that a FcγR (or a region or fragment thereof) resembles or is similar to a human FcγR (i.e., the protein found in the human body) in terms of amino acid sequence and/or structure.

Alternatively, the FcγR "of human origin" can be a recombinant FcγR that is obtained by expression of a recombinant nucleic acid in a host cell, e.g. as described by Sondermann and Jacob (1999), Bioll. Chem. 380(6), 717-721. Briefly, a gene of interest is obtained from an organism and introduced into a vector, e.g. a plasmid or a virus, which is then used to transfer the gene into a host cell which expresses the recombinant gene and produces a recombinant protein product. The person skilled in the art will readily know which host cell to select in order to obtain a FcγR that is e.g. suitable for the preparation of a pharmaceutical composition. For example, in some embodiments, an unglycosylated FcγR may be desired. The person skilled in the art may then select a prokaryotic host cell for expression of the FcγR that is devoid of the enzyme machinery necessary for protein glycosylation. In one embodiment the FcγRs can be expressed in prokaryotes and subsequently purified and refolded according to the description of WO 00/32767.

In another embodiment FcγRs can be easily and unexpensively produced in high purity in eukaryotic expression systems. Useful systems include eukaryotes with a specialized apparatus for the production of extracellular proteins, e.g. B cells. Other possible eukaryotic expression systems include, but are not limited to, CHO or HEK cells. Said soluble FcγR is therefore recombinant, soluble and glycosylated FcγR.

FcγRs as referred to herein further encompass FcγRs that, in comparison to wild type FcγR, have been modified or altered with regard to the amino acid sequence, and include, e.g., additional glycosylation sites or the like. However, also non-glycosylated forms of FcγRs are envisaged and are a preferred embodiment of FcγRs.

The Fcγ receptor of the present invention comprises at least one of the amino acid sequences as shown in SEQ ID NO:1 (amino acid sequence of SM101, also referred to herein as variant3). The FcγR of the present invention is encoded by at least one of a nucleic acid sequence according to SEQ ID NO:6 (nucleic acid sequence coding SM101, also referred to herein as variant3). These sequences can be cloned in an expression vector to produce the corresponding FcγR by recombinant expression.

The present invention also relates to a vector comprising the nucleic acid sequence which encodes the protein according to SEQ ID NO: 1. Such a vector may be, e.g., a plasmid, cosmid, virus, bacteriophage or another vector used e.g. conventionally in genetic engineering, and may comprise further genes such as marker genes which allow for the selection and/or replication of said vector in a suitable host cell and under suitable conditions. In a preferred embodiment, said vector is an expression vector, in which the nucleic acid molecule of the present invention is operatively linked and to expression control sequence(s) allowing expression in prokaryotic or eukaryotic host cells as described herein. The term "operatively linked", as used in this context, refers to a linkage between one or more expression control sequences and the coding region in the polynucleotide to be expressed in such a way that expression is achieved under conditions compatible with the expression control sequence.

The nucleic acid molecules of the present invention may thus be inserted into several commercially available vectors. Nonlimiting examples include plasmid vectors compatible with mammalian cells, such as pUC, pBluescript (Stratagene), pET (Novagen), pREP (Invitrogen), pCRTopo (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pUCTag, pIZD35, pLXIN and pSIR (Clontech) and pIRES-EGFP (Clontech). Preferably, the nucleic acid molecules of the present invention are inserted into the vector "pET" under the control of the IPTG inducible T7-Promoter. Baculovirus vectors such as pBlueBac, BacPacz Baculovirus Expression System (CLONTECH), and MaxBac™ Baculovirus Expression System, insect cells and protocols (Invitrogen) are available commercially and may also be used to produce high yields of biologically active protein. (see also, Miller (1993), Curr. Op. Genet. Dev., 3, 9; O'Reilly, Baculovirus Expression Vectors: A Laboratory Manual, p. 127). In addition, prokaryotic vectors such as pcDNA2; and yeast vectors such as pYes2 are nonlimiting examples of other vectors suitable for use with the present invention.

Other preferred expression vectors of the present application are those for expressing proteins in *Drosophila* cells which are well known in the art, such as the DES2-series of Invitrogen. Preferably, said *Drosophila* cell expression vector is pMTBiP/V5-His B (Invitrogen). The pMT/BiP/V5-His vector offers the following additional features. It has a small size (3.6 kb) to improve DNA yields and increase subcloning efficiency, it has a C-terminal V5 epitope tag for rapid detection with Anti-V5 Antibody and it has a C-terminal 6×His tag for simple purification of recombinant fusion proteins using nickel-chelating resin.

For vector modification techniques, see Sambrook and Russel (2001), loc. cit. Vectors can contain one or more replication and inheritance systems for cloning or expression, one or more markers for selection in the host, e. g., antibiotic resistance, and one or more expression cassettes.

The coding sequences inserted in the vector can be synthesized by standard methods, isolated from natural sources, or prepared as hybrids. Ligation of the coding sequences to transcriptional regulatory elements (e. g., promoters, enhancers, and/or insulators) and/or to other amino acid encoding sequences can be carried out using established methods.

Furthermore, the vectors may, in addition to the nucleic acid sequences of the invention, comprise expression control elements, allowing proper expression of the coding regions in suitable hosts. Such control elements are known to the artisan and may include a promoter, translation initiation codon, translation and insertion site or internal ribosomal entry sites (IRES) (Owens, Proc. Natl. Acad. Sci. USA 98 (2001), 1471-1476) for introducing an insert into the vector. Preferably, the nucleic acid molecule of the invention is operatively linked to said expression control sequences allowing expression in eukaryotic or prokaryotic cells.

Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor lalpha-promoter, CMV enhancer, CaM-kinase promoter or SV40-enhancer.

For the expression in prokaryotic cells, a multitude of promoters including, for example, the tac-lac-promoter, the lacUV5 or the trp promoter, has been described. Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11.

An expression vector according to this invention is at least capable of directing the replication, and preferably the expression, of the nucleic acids and protein of this invention. Suitable origins of replication include, for example, the Col E1, the SV40 viral and the M 13 origins of replication. Suitable promoters include, for example, the cytomegalovirus (CMV) promoter, the lacZ promoter, the gal10 promoter and the *Autographa californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Examples of selectable markers include neomycin, ampicillin, and hygromycin resistance and the like, preferably kanamycin. Specifically-designed vectors allow the shuttling of DNA between different host cells, such as bacteria-yeast, or bacteria-animal cells, or bacteria-fungal cells, or bacteria invertebrate cells.

Beside the nucleic acid molecules of the present invention, the vector may further comprise nucleic acid sequences encoding for secretion signals. Such secretion signal sequences are well known to the person skilled in the art. Furthermore, depending on the expression system used leader sequences capable of directing the expressed polypeptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a part thereof, into, inter alia, the extracellular membrane. Optionally, the heterologous sequence can encode a fusion protein including a C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the proteins, antigenic fragments or fusion proteins of the invention may follow. Of course, the vector can also comprise regulatory regions from pathogenic organisms.

The vector may preferably be an inducible expression vector e.g. an IPTG-inducible vector.

Furthermore, said vector may also be, besides an expression vector, a gene transfer and/or gene targeting vector. Gene therapy, which is based on introducing therapeutic genes (for example for vaccination) into cells by ex-vivo or in-vivo techniques, is one of the most important applications of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957; Schaper, Current Opinion in Biotechnology 7 (1996), 635-640 or Verma, Nature 389 (1997), 239-242 and references cited therein.

The nucleic acid molecules of the invention and vectors as described herein above may be designed for direct introduction or for introduction via liposomes, or viral vectors (e.g. adenoviral, retroviral) into the cell. Additionally, baculoviral systems or systems based on vaccinia virus or Semliki Forest Virus can be used as eukaryotic expression system for the nucleic acid molecules of the invention. In addition to recombinant production, fragments of the protein, the fusion protein or antigenic fragments of the invention may be produced by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule.

The present invention also relates to a host cell comprising the nucleic acid sequence which encodes the protein according to SEQ ID NO: 1 or the vector comprising the nucleic acid sequence which encodes the protein according to SEQ ID NO: 1.

Said "host", may be produced by introducing said vector or nucleotide sequence into a host cell which upon its presence in the cell mediates the expression of a protein encoded by the nucleotide sequence of the invention or comprising a nucleotide sequence or a vector according to the invention wherein the nucleotide sequence and/or the encoded polypeptide is foreign to the host cell. The term "host" when used herein includes host cells.

By "foreign" it is meant that the nucleotide sequence and/or the encoded polypeptide is either heterologous with respect to the host, this means derived from a cell or organism with a different genomic background, or is homologous with respect to the host but located in a different genomic environment than the naturally occurring counterpart of said nucleotide sequence. This means that, if the nucleotide sequence is homologous with respect to the host, it is not located in its natural location in the genome of said host, in particular it is surrounded by different genes. In this case the nucleotide sequence may be either under the control of its own promoter or under the control of a heterologous promoter. The location of the introduced nucleic acid molecule or the vector can be determined by the skilled person by using methods well-known to the person skilled in the art, e.g., Southern Blotting. The vector or nucleotide sequence according to the invention which is present in the host may either be integrated into the genome of the host or it may be maintained in some form extrachromosomally. In this respect, it is also to be understood that the nucleotide sequence of the invention can be used to restore or create a mutant gene via homologous recombination.

In one embodiment, the host cell comprising the nucleic acid sequence which encodes the protein according to SEQ ID NO: 1 or the vector comprising the nucleic acid sequence which encodes the protein according to SEQ ID NO: 1 is a prokaryotic or eukaryotic host cell. Preferably, the prokaryotic host cell is E. coli, more preferably E. coli BL21, such as BL21 (DE3).

Suitable prokaryotic/bacterial cells are those generally used for cloning like E. coli, Salmonella typhimurium, Serratia marcescens or Bacillus subtilis. Said eukaryotic host may be a mammalian cell, an amphibian cell, a fish cell, an insect cell, a fungal cell, a plant cell or a bacterial cell (e.g., E. coli strains HB101, DH5a, XL1 Blue, Y1090 and JM101). Prokaryotic recombinant host cells are preferred, with E. coli being most preferred.

Further examples of eukaryotic host cells include, but are not limited to, yeast, e.g., Saccharomyces cerevisiae, Schizosaccharomyces pombe, Kluyveromyces lactis or Pichia pastoris cells, cell lines of human, bovine, porcine, monkey, and rodent origin, as well as insect cells, including but not limited to, Spodoptera frugiperda insect cells and Drosophila-derived insect cells as well as zebra fish cells. Mammalian species-derived cell lines suitable for use and commercially available include, but are not limited to, L cells, CV-1 cells, COS-1 cells (ATCC CRL 1650), COS-7 cells (ATCC CRL 1651), HeLa cells (ATCC CCL 2), C1271 (ATCC CRL 1616), BS-C-1 (ATCC CCL 26) and MRC-5 (ATCC CCL 171).

Said Drosophila-derived cells can be Drosophila S2 (ATCC CRL-1963) which are, preferably used for heterologous protein expression in Drosophila expression systems, for example, the Drosophila Expression System (DES®).

Mammalian species-derived cell lines suitable for use and commercially available include, but are not limited to, L cells, CV-1 cells, COS-1 cells (ATCC CRL 1650), COS-7 cells (ATCC CRL 1651), HeLa cells (ATCC CCL 2), C1271 (ATCC CRL 1616), BS-C-1 (ATCC CCL 26) and MRC-5 (ATCC CCL 171).

In another more preferred embodiment said amphibian cell is an oocyte. In an even more preferred embodiment said oocyte is a frog oocyte, particularly preferred a Xenopus laevis oocyte.

In a more preferred embodiment, the host according to the invention is a non-human transgenic organism. Said non-human organism may be a mammal, amphibian, a fish, an insect, a fungus or a plant. Particularly preferred non-human transgenic animals are Drosophila species, Caenorhabditis elegans, Xenopus species, zebra fish, Spodoptera frugiperda, Autographa californica, mice and rats. Transgenic plants comprise, but are not limited to, wheat, tobacco, parsley and Arabidopsis.

Transgenic fungi are also well known in the art and comprise, inter alia, yeasts, like S. pombe or S. cerevisae, or Aspergillus, Neurospora or Ustilago species or Pichia species.

The present invention further relates to a protein obtained or obtainable by expression of the nucleic acid sequence which encodes a protein according to SEQ ID NO: 1 or the vector comprising the nucleic acid sequence which encodes a protein according to SEQ ID NO: 1 in a host cell, preferably a prokaryotic host cell, more preferably in E. coli, most preferably in E. coli BL21, such as E. coli BL21 (D3).

Method for producing the polypeptide encoded by a nucleic acid molecule of the invention comprising culturing/raising the host of the invention and isolating the produced polypeptide are described herein.

A large number of suitable methods exist in the art to produce polypeptides in appropriate hosts. If the host is a unicellular organism or a mammalian or insect cell, the person skilled in the art can revert to a variety of culture conditions that can be further optimized without an undue burden of work. Conveniently, the produced protein is harvested from the culture medium or from isolated (biological) inclusion bodies by established techniques. Furthermore, the produced polypeptide may be directly isolated from the host cell. Said host cell may be part of or derived from a part of a host organism, for example said host cell may be part of the tissue, e.g. CNS, skin etc. of an animal or the harvestable part of a plant. Additionally, the produced polypeptide may be isolated from fluids derived from said host, like blood, milk or cerebrospinal fluid.

Additionally the present invention relates to polypeptides which are encoded by the nucleic acid sequence which encodes the protein according to SEQ ID NO: 1 of the invention.

The polypeptide of the invention may accordingly be produced by microbiological methods or by transgenic mammals. It is also envisaged that the polypeptide of the invention is recovered from transgenic plants. Alternatively, the polypeptide of the invention may be produced synthetically or semi-synthetically.

For example, chemical synthesis, such as the solid phase procedure described by Houghton Proc. Natl. Acad. Sci. USA (82) (1985), 5131-5135, can be used. Another method is in vitro translation of mRNA. A preferred method involves the recombinant production of protein in host cells as described above. For example, nucleotide acid sequences comprising all or a portion of any one of the nucleotide sequences according to the invention can be synthesized by PCR, inserted into an expression vector, and a host cell transformed with the expression vector. Thereafter, the host cell is cultured to produce the desired polypeptide, which is isolated and purified. Protein isolation and purification can be achieved by any one of several known techniques; for example and without limitation, ion exchange chromatography, gel filtration chromatography and affinity chromatography, high pressure liquid chromatography (HPLC), reversed phase HPLC, preparative disc gel electrophoresis.

In addition, cell-free translation systems can be used to produce the polypeptides of the present invention. Suitable cell-free expression systems for use in accordance with the present invention include rabbit reticulocyte lysate, wheat germ extract, canine pancreatic microsomal membranes, E. coli S30 extract, and coupled transcription/translation systems such as the TNT-system (Promega). These systems allow the expression of recombinant polypeptides or peptides upon the addition of cloning vectors, DNA fragments, or RNA sequences containing coding regions and appropriate promoter elements. As mentioned supra, protein isolation/purification techniques may require modification of the proteins of the present invention using conventional methods. For example, a histidine tag can be added to the protein to allow purification on a nickel column. Other modifications may cause higher or lower activity, permit higher levels of protein production, or simplify purification of the protein. Other tags include also the flag-tag. Such tags are preferably used for eukaryotic hosts.

The protein of the present invention has preferably the amino acid sequence encoded by a nucleic acid molecule of the present invention as described herein or is obtained or obtainable by expressing said nucleic acid sequence which is described herein. As such also vectors comprising the SEQ ID NO: 1 such as e.g. in expression vectors, can be utilized to achieve expression of a protein obtained or obtainable by expression of the nucleic acid sequence of SEQ ID NO: 1.

For example, E. coli strains BL21 (DE3) can be utilized to mediate the expression of the protein of SEQ ID NO: 1 or the vector comprising the nucleic acid sequence which encodes the protein according to SEQ ID NO: 1. The construction of a vector e.g. for expression under the control of the IPTG inducible T7-Promoter is known in the art. Electrocompetent *E. coli* BL21(DE3) cells can be transformed with plasmid DNA e.g. an expression vector as described above. The processed cells are then grown in medium. After cultivation, cells are harvested by centrifugation or can directly be lysated e.g. by sonification and the suspension is then centrifuged or treated as exemplified in the example. The pellet, i.e. the crude inclusion bodies, can then be resuspended in buffer e.g. lysis buffer. The wet inclusion bodies are then solubilized. After another centrifugation the protein of interest can be obtained or before that the protein can be refolded e.g. as exemplified in the example. Protein expression, cell disruption, recovery of inclusion bodies, and refolding of inclusion bodies is typically done as is known in the art and, e.g., described herein in the Examples.

One way to purify a protein includes ammonium sulfate precipitation as this is a method used to purify proteins by altering their solubility. It is a specific case of a more general technique known as salting out. Ammonium sulfate is commonly used as its solubility is so high that salt solutions with high ionic strength are allowed. The solubility of proteins varies according to the ionic strength of the solution, and hence according to the salt concentration. Two distinct effects are observed: at low salt concentrations, the solubility of the protein increases with increasing salt concentration (i.e. increasing ionic strength), an effect termed salting in. As the salt concentration (ionic strength) is increased further, the solubility of the protein begins to decrease. At sufficiently high ionic strength, the protein will be almost completely precipitated from the solution (salting out).

Since proteins differ markedly in their solubilities at high ionic strength, salting-out is a very useful procedure to assist in the purification of a given protein. By addition of kosmotropic ammonium sulfate folding byproducts like unfolded and misfolded species but also host cell derived impurities like cell wall components and proteins are precipitated. With increasing precipitant concentration the precipitation efficiency will be increased and hence a highly purified FcR preparation is obtained as long as the FcR variant is resistant to precipitation at such high ammonium sulfate concentrations. Therefore it is desirable to have a FcR variant which is highly soluble at ammonium sulfate concentrations equal to or even exceeding 1.5 M.

The precipitated protein is then removed by centrifugation and then the ammonium sulfate concentration is increased to a value that will precipitate most of the protein of interest whilst leaving the maximum amount of protein contaminants still in solution. The precipitated protein of interest is recovered by centrifugation and dissolved in fresh buffer for the next stage of purification.

Preferably, the protein of the present invention has a high solubility at ammonium sulfate concentrations equal to or exceeding 1.5 M.

The present invention further relates to a protein which is encoded by a nucleic acid sequence according to SEQ ID NO: 6.

A protein according to SEQ ID NO: 2, 3, 4, 5, or 9 can be encoded by the nucleic acid sequence according to SEQ ID NO: 6, wherein
(i) the first codon (ATG) is omitted from SEQ ID NO: 6 which results in a protein according to SEQ ID NO: 2,
(ii) the first (ATG) and the second codon (GCA) are omitted from SEQ ID NO: 6 which results in a protein according to SEQ ID NO: 3,
(iii) the first (ATG), second (GCA) and third codon (CCG) are omitted from SEQ ID NO: 6 which results in a protein according to SEQ ID NO: 4,
(iv) the first (ATG), second (GCA), third (CCG), fourth (CCG) and fifth (AAA) codon are omitted from SEQ ID NO: 6 which results in a protein according to SEQ ID NO: 5,
(v) codons encoding from N- to C-Terminus the amino acids TPA are added between the first (ATG) and second (GCA) codon from of SEQ ID NO: 6 and codons encoding the amino acid sequence MGI are added 3' to the penultimate codon (CCG) from SEQ ID NO: 6 which results in a protein according to SEQ ID NO: 9.

The present invention also relates to a pharmaceutical composition comprising the protein obtained or obtainable by expression of the nucleic acid which encodes the protein according to SEQ ID NO: 1 or the vector comprising the nucleic acid which encodes the protein according to SEQ ID NO: 1 or a protein encoded by the nucleic acid sequence of SEQ ID NO: 6.

The term "composition", as used in accordance with the present invention, relates to
(a) composition(s) which comprise(s) at least one protein obtained or obtainable by expression of the nucleic acid which encodes the protein according to SEQ ID NO: 1;
(b) or the vector comprising the nucleic acid which encodes the protein according to SEQ ID NO: 1, 2, 3, 4, 5, or 9;
(c) or a protein encoded by the nucleic acid sequence of SEQ ID NO: 6;
(d) or a nucleic acid sequence which encodes the protein according to SEQ ID NO: 1, 2, 3, 4, 5 or 9.

It is envisaged that the compositions of the present invention which are described herein below comprise the aforementioned proteins in any combination. It may, optionally, comprise further molecules which are capable of binding other proteins e.g. antibodies or lymphocytes. The composition may be in solid, liquid or gaseous form and may be, inter alia, in the form of (a) powder(s), (a) tablet(s), (a) solution(s) (an) aerosol(s), granules, pills, suspensions, emulsions, capules, syrups, liquids, elixirs, extracts, tincture or fluid extracts or in a form which is particularly suitable for oral or parental or topic administration.

Another preferred composition of the present invention is a pharmaceutical composition optionally further comprising a pharmaceutical acceptable carrier and/or excipient. Said pharmaceutical composition comprises, inter alia, the nucleic acid sequence of the present invention or the polypeptide of the present invention which may be coupled to a further polypeptide, for example an antibody or another protein present in the serum.

The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans.

The term "carrier" refers to a diluent, adjuvant, or vehicle with which the pharmaceutical composition is administered. Such pharmaceutical carriers can be sterile liquids, such as water and oils. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the aforementioned compounds, preferably in purified form, together with a suitable amount of carrier so as to provide the form for proper administration to the subject. The formulation should suit the mode of administration.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Effective doses may be extrapolated from dose-response curves derived from in vitro or animal model test systems. Preferably, the pharmaceutical composition is administered directly or in combination with an adjuvant.

The pharmaceutical composition can be designed for the application in gene therapy. The technique of gene therapy has already been described above in connection with the host cells of the invention and all what has been said there also applies in connection with the pharmaceutical composition. For example, the nucleic acid molecule or the protein comprising the protein obtained or obtainable by expression of the nucleic acid of SEQ ID NO: 1 or the vector comprising the nucleic acid which encodes the protein according to SEQ ID NO: 1 or a protein encoded by the nucleic acid sequence of SEQ ID NO: 6 in the pharmaceutical composition is preferably in a form which allows its introduction, expression and/or stable integration into cells of an individual subject to be treated.

For gene therapy, various viral vectors which can be utilized, for example, adenovirus, herpes virus, vaccinia, or, preferably, an RNA virus such as a retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can also incorporate multiple genes. All of these vectors can transfer or incorporate a gene for a selectable marker so that transduced cells can be identified and generated. Retroviral vectors can be made target specific by inserting, for example, a polynucleotide encoding a sugar, a glycolipid, or a protein. Those of skill in the art will know of, or can readily ascertain without undue experimentation, specific polynucleotide sequences which can be inserted into the retroviral genome to allow target specific delivery of the retroviral vector containing the inserted polynucleotide sequence.

Since recombinant retroviruses are preferably defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to w2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium. Another targeted delivery system for the nucleic acid molecules of the present invention is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 pm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity;

(2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries.

In the context of the present invention the term "subject" means an individual in need of a treatment of an affective disorder. Preferably, the subject is a vertebrate, even more preferred a mammal, particularly preferred a human. In one embodiment, the human is a patient or an individual.

The term "administered" means administration of a therapeutically or diagnostically effective dose of the aforementioned nucleic acid molecule encoding the polypeptide of the present invention to an individual.

As used herein, a "therapeutically effective amount" refers to an amount of the therapeutic active component or agent which is sufficient to treat or ameliorate a disease or disorder, to delay the onset of a disease or provides any therapeutical benefit in the treatment or management of a disease.

As is known in the art and described above, adjustments for systemic versus localized delivery, age, body weight, general health, sex, diet, time of administration, drug interaction and the severity of the condition may be necessary, and will be ascertainable with routine experimentation by those skilled in the art. The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intra-arterial, intranodal, intramedullary, intrathecal, intraventricular, intranasally, intrabronchial, transdermally, intranodally, intrarectally, intraperitoneally, intramuscularly, intrapulmonary, vaginally, rectally, or intraocularly. In some instances, for example, in the treatment of wounds and inflammation, the candidate agents may be directly applied as a solution dry spray.

The pharmaceutical composition is preferably injected. This injection is administered using intravenous infusions, subcutaneously or intramuscular. Further the pharmaceutical composition may comprise other pharmaceutically acceptable carriers and/or excipients. The term "pharmaceutically acceptable" means generally recognized pharmacopoeia for use in animals, and more particularly in humans.

Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Furthermore, the pharmaceutical composition may be administered in combination with one or more other therapeutic agent or antibody, such as steroids or intravenous immunoglobulin, in particular corticosteroids, glucocorticoid prodrugs, e.g. prednisone, IVIG, anti-D, vinca alkaloids, e.g. vincristine or vinblastine, danazol, immunosuppressive agents, e.g. azathioprine, cyclophosphamide or cyclosporin A, dapsone, thrombopoicetic agents, rituximab, mycophenolate mofetil, romiplostim, eltrombopag, mycophenolate mofetil. As used herein, the term "in combination" refers to the use of more than one prophylactic and/or therapeutic agent. The use of the term "in combination" does not restrict the order in which prophylactic and/or therapeutic agents are administered to a patient.

The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition. Dosages will vary but a preferred dosage for intravenous administration of DNA is from approximately $10^6$ to $10^{12}$ copies of the DNA molecule. If the regimen is a continuous infusion, it should also be in the range of 1 µg to 10 mg units per kilogram of body weight per minute, respectively. Progress can be monitored by periodic assessment. The pharmaceutical composition of the invention may be administered locally or systemically. Administration will preferably be parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium ion solution, Ringer's dextrose, dextrose and sodium ion, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

It is also envisaged that the pharmaceutical compositions are employed in co-therapy approaches with other agents, for example, useful in detecting methylated DNA and, thus, for example, useful in diagnosing malignancies which may show a typical methylated pattern.

The present invention provides kits that can be used for the above described methods. It is also well known by a person skilled in the art that the pharmaceutical composition can be in the form of a multiple-dosage-kit containing sufficient amounts of administration doses of FcγR for effectively treating or preventing inflammatory diseases and/or autoimmune diseases in a patient. In one embodiment, the pharmaceutical pack or kit comprises one or more containers filled with the pharmaceutical composition of the invention. Furthermore, one or more additional prophylactic or therapeutic agents useful for the treatment of a disease can also be included in the pharmaceutical pack or kit.

In addition, the pharmaceutical composition of the present invention can be used for the treatment and prevention of disorders or diseases.

As used herein, the term "treating" and analogous terms refer to a management and care of a patient and/or the combating of disease or disorder. As used herein, the terms "prevent", "preventing" and "prevention" refer to the prevention of the recurrence or onset of one or more symptoms of a disorder in a subject resulting from the administration of a prophylactic or therapeutic agent.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

In a preferred embodiment the inflammatory disease which can be treated by the present method is Primary Immune Thrombocytopenia (ITP), Systemic Lupus Erythematosus (SLE), Rheumatoid Arthritis (RA), or Autoimmune Haemolytic Anaemia (AIHA).

The present invention also relates to a composition of matter comprising a protein according to SEQ ID No: 2 and/or 3.

The term "composition of matter" means all compositions of two or more substances and all composite substances, whether they are the result of chemical union, or of mechanical mixture, or a biological product. A composition of matter can be formed by the mixture of two or more ingredients. The mixture of ingredients in a composition of matter may be produced by mechanical or chemical operations or by biological processes.

The composition of matter can comprise 1, 2, 3, 4, 5, 6, 7, 8, 9, 10 or more active ingredients. With "active ingredient" a therapeutically effective ingredient is meant. Such an active ingredient can bind to the IgG antibodies as described herein and possibly can bind to lymphocytes, e.g. T-cells, B-cells, natural killer cells. Such an active ingredient only binds to the constant region. It is preferred that in a composition of matter a protein of the present invention is the sole active ingredient as described above.

In one embodiment the composition of matter comprises a protein according to SEQ ID No: 2 and 3. In another embodiment the composition of matter comprises a protein according to SEQ ID No: 2 or 3. In another embodiment the composition of matter comprises a protein according to SEQ ID No: 2. In another embodiment the composition of matter comprises a protein according to SEQ ID No: 3.

In one embodiment the composition of matter of the present invention further comprises a protein according to SEQ ID No. 4 and/or 5. In another embodiment the composition of matter of the present invention further comprises a protein according to SEQ ID No. 4 and 5. In another embodiment the composition of matter of the present invention further comprises a protein according to SEQ ID No. 4 or 5. In another embodiment the composition of matter of the present invention further comprises a protein according to SEQ ID No. 4. In another embodiment the composition of matter of the present invention further comprises a protein according to SEQ ID No. 5.

In another embodiment the composition of matter of the present invention is characterized in that the amount of the protein according to SEQ ID No: 2 exceeds that of the protein according to SEQ ID No: 3.

In another embodiment the composition of matter of the present invention is characterized in that the amount of the protein according to SEQ ID No: 3 exceeds that of the protein according to SEQ ID No: 2.

In another embodiment the composition of matter of the present invention is characterized in that the amount of the protein according to SEQ ID No: 2 exceeds that of the protein according to SEQ ID No: 3 and the amount of the proteins according to SEQ ID No: 2 and 3 exceeds that of the protein according to SEQ ID No: 4 and/or 5.

In one embodiment the composition of matter comprises a protein according to SEQ ID No: 9.

The composition of matter is in a preferred embodiment a pharmaceutical composition.

The present invention also relates to a method of manufacturing a pharmaceutical composition comprising culturing the host cell of the present invention under conditions allowing the expression of the encoded protein, and recovering the obtained pharmaceutical composition.

EXAMPLES

The following examples illustrate the invention. These examples should not be construed as to limit the scope of this invention. The examples are included for purposes of illustration and the present invention is limited only by the claims.

Materials and Methods

Production of FcR Variants 75 mL LB supplemented with 50 µg/mL Kanamycin in a 250 mL baffled conical flask were inoculated with 5 µL of a glycerol stock and shaken for 15 h at 37° C., 170 rpm (Multitron Standard, Infors HT). Subsequently 1 µL LB in a 2 L baffled conical flask was inoculated with 10 mL of the overnight culture and shaken at 37° C., 170 rpm. At an $OD_{600}$ of 1.6, the expression was induced by addition of 1 mM IPTG. After cultivation for another 3 h at 37° C., 170 rpm the cells were harvested by centrifugation (10 min at 5'000·g, 4° C.), washed once with 200 mL ice-cold PBS and stored at −20° C.

Cell Disruption and Isolation of Inclusion Bodies 6-8 g frozen E. coli cells were thawed at room temperature and resuspended in 30 mL lysis buffer (50 mM Tris/HCl, 25 mM NaCl, 2 mM EDTA, pH 8.0) supplemented with 100 µg/mL lysozyme using a teflon-in-glass homogenizer. After incubation for 15 min on ice the cells were disrupted by sonification (Power setting 6, duty cycle 30%, 30 min, sonifier 250 equipped with a microtip, Branson) and the suspension centrifuged (45 min at 13"000·g, 4° C.). 1 mL of the supernatant was sampled and the remaining liquid discarded. The pellet, i.e. the crude inclusion bodies, were resuspended in 35 mL lysis buffer supplemented with 0.5% (v/v) Polysorbate 20 using a teflon-in-glass homogenizer and centrifuged (15 min at 13"000·g, 4° C.). After one additional wash step with detergent, a final wash-step was performed using lysis buffer alone. The washed inclusion bodies were stored at −20° C. until use.

Refolding and Purification of FcR Variants

Wet inclusion bodies were solubilised at 200 mg/mL in 20 mM Tris/HCl, 6 M guanidine, 3 mM EDTA, 5 mM DTT, pH 8.0 for 2.5 h at 20° C. under constant stirring (400 rpm) in a closed centrifuge tube. After centrifugation (20'000·g, 10 min, 20° C.) the supernatant was collected by decantation and the FcR content was determined after 1:60 dilution by RP-HPLC on Knauer Bioselect C4. Based on the analytical results, the solubilised inclusion bodies were diluted with 20 mM Tris/HCl, 6 M guanidine, 3 mM EDTA, 5 mM DTT, pH 8.0 to a FcR content of 21 mg/mL and one part of the diluted FcR solution was added dropwise to 20 parts stirred (800 rpm) refolding buffer (20 mM Tris/HCl, 2 M urea, 0.5 M arginine, 2 mM cysteamine, 2 mM cystamine, pH 7.7 at 6° C.). After incubation for 16 h at 10° C. in a sealed container without stirring, the refolding solution was warmed to room temperature. The warm refolding solution was adjusted to 1.1 M $(NH_4)_2SO_4$ by dropwise addition of 3.5 M $(NH_4)_2SO_4$, 20 mM $NH_4H_2PO_4$, pH 7.0 under constant stirring (400 rpm). After stirring for another 1 h at 200 rpm the suspension was centrifuged (20'000·g, 20 min, 20° C.), the supernatant filtered (0.2 µm Durapore, Millipore) and the filtrate was loaded at 4 mL/min, 4 mg protein/mL resin onto a 35 mL Phenyl Sepharose HP column (h=6.6 cm, d=2.6 cm, GE Healthcare) equilibrated in 1.2 M $(NH_4)_2SO_4$, 20 mM $NH_4H_2PO_4$, pH 7.0. The column was washed with 100 mL 1.2 M $(NH_4)_2SO_4$, 20 mM $NH_4H_2PO_4$, pH 7.0 and bound protein was eluted with a 350 mL linear gradient from 1.2 M to 0 M $(NH_4)_2SO_4$ in 20 mM $NH_4H_2PO_4$, pH 7.0 at 5 mL/min. The eluate was collected in 7.5 mL fractions, which were subjected to RP-HPLC analysis on Phenomenex Jupiter C4. Fractions with a purity above 85% in respect to the FcR variant sought-after were pooled, concentrated approx. two times and diafiltered against 20 mM L-histidine pH 6.5 by tangential flow filtation (Vivaflow 50, 5 kDa MWCO, 0.01 m², cross-flow 200 mL/min, pIN=2 bar; Sartorius) until the conductivity was reduced to approx. 5 mS/cm. After the buffer exchange the solution was loaded at 2 mL/min, 20 mg protein/mL resin onto a 9 mL SP Sepharose HP column (h=4.5 cm, d=1.6 cm, GE Healthcare) equilibrated in 20 mM L-histidine, pH 6.5. The column was washed with 30 mL 20 mM L-histidine, 30 mM NaCl, pH 6.5 and bound protein was eluted with a 90 mL linear gradient from 20 mM to 400 mM NaCl in 20 mM L-histidine, pH 6.5 at 3 mL/min. Fractions comprising the main peak were pooled, adjusted to 15.4 mS/cm with 20 mM L-histidine pH 6.5, concentrated to approx. 20 mg/mL by ultrafiltration (4'000·g, 5 kDa MWCO, Vivaspin 20, Sartorius) and diluted to 15 mg/mL with 20 mM NaCl, 150 mM NaCl, pH 6.5. The diluted FcR solution was filtered (0.45 µm PES membrane, Puradisc™ 25 mm, Whatman) aliquoted, snap frozen in liquid nitrogen and stored at −80° C.

Precipitation Screen

FcR was adjusted to 0.7 mg/mL in the presence of 20 mM histidine, 150 mM NaCl and 0-2.8 M ammonium sulfate by addition of the appropriate amount of ddH2O, 10× histidine/NaCl stock solution (200 mM histidine, 1.5 M NaCl) and ammonium sulfate stock solution (4M in ddH2O). The pH was set to 6, 7 or 8 by using a 10× histidine/NaCl and ammonium sulfate stock at the appropriate pH. Each condition was set up in duplicate. The samples were incubated for 1 h at 25° C., centrifuged (20'000×g, 10 min) and 30 µL of the supernatant was transferred to a 384 well plate (uclear, non-binding, black, Greiner Bio-one). The absorbance at 280 nm was measured (Spectrofluor plus, Tecan) and the protein content was calculated according to Lambert Beers Law using a mass extinction coefficient of 1.5625 mL×mg−1×cm−1 and a path length of 0.24 cm. The absorbance of a sample well was corrected by the absorbance of a well containing only blank buffer.

SDS Page

To suppress subsequent disulfide exchange, free thiols were alkylated with iodoacetamide by mixing 18 µL solubilised IBs or refolding broth with 2 µL 250 mM freshly prepared iodoacetamide in $H_2O$. The mixture was incubated for 45 min at 30° C., 750 rpm in the dark and directly used for SDS-PAGE sample preparation according to the NuPAGE® Novex® manual (Invitrogen). Proteins were separated on a 4-12% Bis-Tris gel in MES running buffer (both NuPAGE® Novex®, Invitrogen) according to manufacturer's instructions. Gels were washed three times with $ddH_2O$ and stained with Simply Blue™ Safe Stain (Invitrogen) for at least 6 h at room temperature. As molecular weight marker 10 of SeeBlue® Plus2 pre-stained standard (Invitrogen) was applied.

LC-MS

The molecular mass of intact the expressed protein was determined by mass spectrometry in collaboration with the MPI of Biochemistry (Martinsried). Samples were analyzed on an ESI-TOF mass analyzer (microTOF, Bruker) equipped with a Phenomenex Aeris™ Widepore $C_4$ column (100 mm×2.1 mm, 3.6 µM particle size, 300 Å pore size) previously equilibrated in 30% acetonitrile, 0.05% TFA. FcR containing samples were injected at 0.25 mL/min, 20° C. and bound protein was eluted with a 15 min linear gradient from 30% to 80% acetonitrile, 0.05% TFA.

UV/VIS Spectroscopy

If necessary the protein solution was diluted with the respective buffer to an $OD_{280}$ between 0.2 and 0.8. 400 µL of the solution were transferred to a UV-microcuvette (UV-cuvette micro, Brand). The absorbance at 280 nm and 320 nM was recorded (TidasE, J&M Analytik) and protein concentration in mg/mL was calculated according to the following equation:

$$c_{protein} = (OD_{280} - OD_{320}) \times 0.64 \text{ mg/mL}$$

As a blank the respective buffer was used. The assay was carried out in triplicate and the results were averaged.

Example 1

Precipitation Screen

The manufacture of FcR protein by a refolding based process commonly involves an ammonium sulfate precipitation step. By addition of the kosmotropic ammonium sulfate folding byproducts like unfolded and misfolded species but also host cell derived impurities like cell wall components and proteins are precipitated. With increasing precipitant concentration the precipitation efficiency will be increased and hence a highly purified FcR preparation is obtained as long as the FcR variant is resistant to precipitation at such high ammonium sulfate concentrations. Therefore it is desirable to have a FcR variant which is highly soluble at ammonium sulfate concentrations equal to or exceeding 1.5 M. Besides the straightforward precipitation of impurities high ammonium sulfate concentrations will facilitate efficient binding to a HIC resin. As a high dynamic binding capacity is always a key development target for a chromatographic capturing step, solubility in the presence of high ammonium sulfate concentrations is mandatory.

In order to assess the solubility of the FcR variants in the presence of ammonium sulfate each variant was incubated with increasing concentrations of ammonium sulfate at pH 6 to 8. After 1 hour at 25° C. the FcR concentration in the supernatant in was determined by UV/vis spectroscopy. As shown in FIG. 2 variant 3 is most resistant to precipitation by ammonium sulfate with half-maximal precipitation at 2.05 M to 2.13 M $(NH_4)_2SO_4$. On the contrary, "variant 2" (SEQ ID NO: 8) and "variant 4" (SEQ ID NO: 9) are less soluble at high ammonium sulfate concentrations, showing half-maximal precipitation at $(NH_4)_2SO_4$ concentrations in the range 1.70 M-1.76 M. Nevertheless, "variant 4" is still soluble at a high ammonium sulfate concentration. The pH dependence of the solubility was for all FcR variants negligible.

Note that it is not possible to carry out a precipitation screen and, thus, determine the solubility of "variant 1" in high ammonium sulfate concentrations, since "variant 1" does not sufficiently refold and, therefore, no soluble protein can be obtained for the precipitation screen.

The invention claimed is:

1. A vector comprising a nucleic acid which encodes a protein consisting of the amino acid sequence according to SEQ ID NO: 1.

2. An isolated host cell comprising the vector of claim 1.

3. The host cell of claim 2, wherein the host cell is a prokaryotic or eukaryotic host cell.

4. The host cell of claim 2, wherein the host cell is *E. coli*.

5. The host cell of claim 4, wherein the host cell is *E. coli* BL21.

6. A pharmaceutical composition comprising:
a protein obtained or obtainable by expression of a nucleic acid which encodes a protein consisting of the amino acid sequence according to SEQ ID NO:1 or a vector which expresses the protein consisting of the amino acid sequence according to SEQ ID NO:1 in a host cell; and
a pharmaceutically acceptable excipient.

7. The pharmaceutical composition of claim 6, wherein the host cell is a prokaryotic host cell.

8. The pharmaceutical composition of claim 7, wherein the host cell is *E. coli*.

* * * * *